United States Patent [19]
Heusmann et al.

[11] Patent Number: 5,840,035
[45] Date of Patent: Nov. 24, 1998

[54] METHOD FOR THE SPECTROSCOPIC EXAMINATION OF A BIOLOGICAL TISSUE

[75] Inventors: Hans Heusmann, München; Jochen Kölzer, Putzbrunn, both of Germany

[73] Assignee: Siemens Aktiengesellschaft, Munich, Germany

[21] Appl. No.: 875,842

[22] PCT Filed: Feb. 1, 1996

[86] PCT No.: PCT/DE96/00151

§ 371 Date: Aug. 6, 1997

§ 102(e) Date: Aug. 6, 1997

[87] PCT Pub. No.: WO96/24836

PCT Pub. Date: Aug. 15, 1996

[30] Foreign Application Priority Data

Feb. 7, 1995 [DE] Germany ................... 195 04 174.7

[51] Int. Cl.$^6$ ........................................... A61B 6/00
[52] U.S. Cl. ............................................ 600/477
[58] Field of Search ................... 600/476, 477, 600/473, 475, 407, 442, 310, 309; 356/39, 432, 433

[56] References Cited

U.S. PATENT DOCUMENTS

| | | | |
|---|---|---|---|
| 4,655,225 | 4/1987 | Dahne et al. ................... | 600/310 |
| 4,768,516 | 9/1988 | Stoddart et al. ............... | 600/476 |
| 4,805,623 | 2/1989 | Jobsis ........................... | 600/310 |
| 5,099,123 | 3/1992 | Harjunmaa ..................... | 250/345 |
| 5,112,124 | 5/1992 | Harjunmaa et al. ............ | 365/39 |
| 5,119,815 | 6/1992 | Chance ........................... | 600/310 |
| 5,293,873 | 3/1994 | Fang . | |
| 5,492,118 | 2/1996 | Gratton et al. ................. | 600/310 |

FOREIGN PATENT DOCUMENTS

| | | |
|---|---|---|
| 4309531 | 9/1994 | Germany . |
| OS 43 09 531 | 9/1994 | Germany . |

OTHER PUBLICATIONS

Farrell et al., A diffusion theory model of spatially resolved, steady state difuse reflectance for the noninvasive determination of tissue optical properties in vivo, Med. Phys. 19(4), Jul./Aug, pp. 879–888, 1992.

Patterson et al., Time resolved reflectance and transmittance for the non–invasive measurement of tissue optical properties, Applied Optics, vol. 28, No. 12, pp. 2331–2336, Jun. 15, 1989.

Delori et al., Spectral reflectance of the human ocular funds, Applied Optics, vol. 28, No. 6, pp. 1061–1077, Mar. 15, 1989.

(List continued on next page.)

*Primary Examiner*—Brian Casler
*Attorney, Agent, or Firm*—Hill & Simpson

[57] ABSTRACT

In a method for spectroscopic examination of a biological tissue the tissue is irradiated with light having an intensity $I_0(\lambda)$ with the wavelength $\lambda$ being varied, a transmission or reflection spectrum $l(\lambda)$ is obtained by measuring the intensity of the radiation transmitted or reflected by the tissue dependent on the wavelength $\lambda$, and an approximate description of the measured transmission or reflection spectrum $l(\lambda)$ or of the spectrum $l(\lambda)/I_0(\lambda)$ normalized to the incident radiation intensity, or of the quantity $\log\{l(\lambda)/I_0(\lambda)\}$ with an analytical function is made. The analytical function has a Beer-Lambert dependency on a first parameter which describes the absorption properties of the tissue and has a second parameter which is the average path length $L(\lambda)$ of the photons in the tissue, representing a slice thickness. The first parameter is dependent on concentrations $c_i$ of a number i of selected tissue components which are employed as fit parameters, as well as being dependent on specific absorption coefficients $\alpha_i(\lambda)$ according to the relationship $$\mu_a(\lambda) = \sum_i c_i \cdot \alpha_i(\lambda).$$

The identified concentrations $c_1$ are then compared to reference values.

5 Claims, 4 Drawing Sheets

OTHER PUBLICATIONS

"Breast Tumor Characterization Using Near–Infra–Red Spectroscopy, " Kang et al., SPIE, vol. 1888, pp. 487–499.

"Contrast in Diaphanography of the Breast," Navarro et al., Med. Phys. 15 (2), Mar./Apr. 1988, pp. 181–187.

"A Comprehensive Approach To Breast Cancer Detection Using Light: Photon Localization By Ultrasound Modulation and Tissue Characterization by Spectral Discrimination," Marks et al., SPIE, vol. 188, pp. 500–511.

"Introduction: A Medical Perspective at the Threshold of Clinical Optical Tomography," Benaron et al., Medical Optical Tomography. Functional Imaging and Monitoring, The International Institute for Optical Engineering, SPIE, vol. IS11 (1993).

"Time Resolved Reflectance and Transmittance for the Non– invasive Measurement of Tissue Optical Properties," Patterson et al., Applied Optics, vol. 28, No. 12, Jun. 15, 1989, pp. 2331–2335.

"Spectral Reflectance of the Human Ocular Fundus," Delori et al., Applied Optics, vol. 28, No. 6, Mar. 15, 1989, pp. 1061–1077.

"A Diffusion Theory Model of Spatially Resolved, Steady–state Diffuse Reflectance for the Noninvasive Determination of Tissue Optical Properties in vivo" Farrell et al., Med. Phys. vol. 19, No. 4, Jul./Aug. 1992, pp. 879–888.

METHOD FOR THE SPECTROSCOPIC EXAMINATION OF A BIOLOGICAL TISSUE

BACKGROUND OF THE INVENTION

1. Field of the Invention

The present invention is directed to a method for spectroscopic examination of biological tissue.

2. Description of the Prior Art

The diagnosis of mammary carcinoma is currently mainly based on the imaging method of X-ray mammography. Portions of the public and of the medical community, however, are increasingly critical of this examination method since damage to the transirradiated tissue cannot be precluded with certainty. Additionally utilized, further, is the extremely complicated nuclear magnetic resonance tomography as well as, to a slight extent, ultrasound measuring methods and infrared thermography.

Light-tomographic methods are being clinically tested wherein to tissue to be examined is illuminated with visible or, respectively, IR light and the reflected or transmitted radiation is detected (see, for example, G. Muller et al. (Eds.), Medical Optical Tomography. Functional Imaging and Monitoring, The international Institute for Optical Enineering [sic], Bellingham, Wash., 1993, SPIE Vol. IS11; B. Chance, R. R. Alfano, A. Katzir (Eds.) Photon Migration and Imaging in Random Media and Tissues, The International Institute for Optical Engineering, Bellingham, Wash. 1993, SPIE Vol. 1988; G A Navarro, A. E. Profio; Med. Phys. Vol. 15(1988); S. 181–187. Since the measured intensities are dependent on the optical properties of the respectively transirradiated region, one hopes to be able to distinguish tissue types and identify and localize physiological or, respectively, pathological modifications in the tissue. Possible applications of light-tomography extend from the detection of mammary carcinoma via the recognition of Alzheimer's disease up to the registration of the oxygenation of the brain and the extremities.

SUMMARY OF THE INVENTION

An object of the invention is to create an optical method with which physiological and pathological modifications in a biological tissue, particularly in the human body, can be detected in vivo. The method should not produce any damage to the tissue and should be comparatively simple to implement without great apparatus outlay.

The above object is achieved in a method for spectroscopic examination of a biological tissue wherein the tissue is irradiated with light having an intensity $l_0(\lambda)$ with the wavelength $\lambda$ being varied, a transmission or reflection spectrum $l(\lambda)$ is obtained by measuring the intensity of the radiation transmitted or reflected by the tissue dependent on the wavelength $\lambda$, and an approximate description of the measured transmission or reflection spectrum $l(\lambda)$ or of the spectrum $l(\lambda)/l_0(\lambda)$ normalized to the incident radiation intensity, or of the quantity $\log\{l(\lambda)/l_0(\lambda)\}$ with an analytical function is made. The analytical function has a Beer-Lambert dependency on a first parameter which describes the absorption properties of the tissue and has a second parameter which is the average path length $L(\lambda)$ of the photons in the tissue, representing a slice thickness. The first parameter is dependent on concentrations $c_i$ of a number i of selected tissue components which are employed as fit parameters, as well as being dependent on specific absorption coefficients $\alpha_i(\lambda)$ according to the relationship $$\mu_a(\lambda) = \sum_i c_i \cdot \alpha_i(\lambda).$$

The identified concentrations $c_1$ are then compared to reference values.

The method is preferably employed in the area of medical diagnostics. Due to its enhanced sensitivity or, respectively, selectivity compared to what is referred to as diaphanography (see, for example, /3/), regions with pathological tissue modifications can be distinguished better from surrounding, healthy tissue and carcinoma in the female breast can be more exactly localized.

DESCRIPTION OF THE PREFERRED EMBODIMENT

Figure 1:
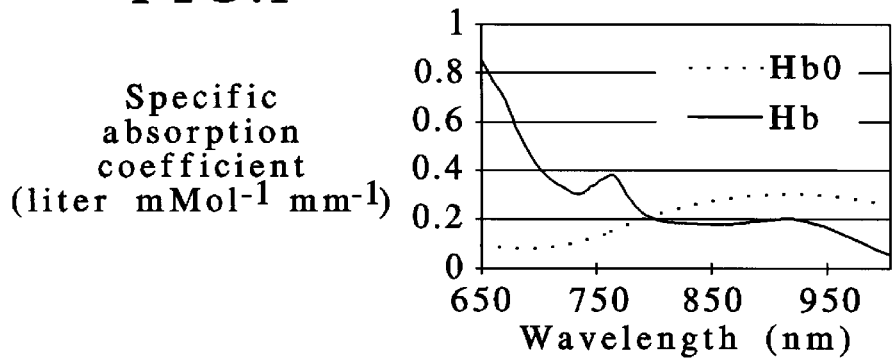
FIGS. 1 and 2 show the absorption coefficients of hemoglobin ($H_b$), oxyhemoglobin ($H_bO$), water and fat (vegetable oil) dependent on wavelength.

The invention strives to describe the transmission spectra of the female breast measured in vivo by an analytical function $l(\lambda)$, whereby the following, highly simplified model assumptions form the basis:

1) the breast tissue is composed of a uniform mixture of the absorbers water, fat, Hb and HbO;
2) the sum of the volume parts of water and fat amounts to 100%;
3) the volume parts of Hb and HbO are left out of consideration (2.3 mMol per liter of blood).

In an exclusively absorbent medium, the attenuation of a light ray exhibiting the initial intensity $l_0$ is described by the Beer-Lambert law $$l = l_0 \cdot \exp\{-\mu_a \cdot d\} \qquad (1)$$

whereby d references the thickness of the transirradiated slice and $\mu_a$ references the absorption coefficient of the medium. When the medium is composed of a plurality of absorbers, then the absorption coefficient $\mu_a$ is calculated from the sum of the products of the absorber concentrations $c_i$ and the specific absorption coefficients $\alpha_i$ as $$\mu_a := \sum_i c_i \cdot \alpha_i \qquad (2)$$

In the case of a tissue composed of the above-recited components, $\mu_a$ is thus established by $$\mu_a = C_{water} \cdot \alpha_{water} + C_{fat} \cdot \alpha_{fat} + C_{Hb} \cdot \alpha_{Hb} + C_{HbO} \cdot \alpha_{HbO} \qquad (3)$$

Equation (1), however, is not valid for highly scattering media since the path lengths covered by the individual photons in the medium are not known here. Patterson et al. Appl. Optics, Vol. 28 (1988), pp 2331–2336, however, have solved the diffusion equation for a plane-parallel geometry and calculated the average path length $L(\lambda)$ of the photons in a scattering medium as $$L = \left( \frac{4\mu_a}{3(\mu_a + \mu'_s)} \right)^{-1/2} \frac{\left( d - \frac{1}{\mu'_s} \right) \exp\left( \frac{2}{\mu'_s} \sqrt{\mu_a 3(\mu_a + \mu'_s)} \right) - \left( d + \frac{1}{\mu'_s} \right)}{\exp\left( \frac{2}{\mu'_s} \sqrt{\mu_a 3(\mu_a + \mu'_s)} \right) - 1} \quad (4)$$

whereby $\mu'_s$ references the wavelength-dependent, reduced scatter coefficient of the medium. When the thickness d in the Beer-Lambert law is then replaced by the wavelength-dependent average path length $L(\lambda)$ of the photons and wavelength-independent correction factors $x_1$, $x_2$ are introduced, then the transmitted intensity $l(\lambda)$ can be written as $$l(\lambda) = l_0(\lambda) \cdot x_1 \cdot \exp\{-\mu_s(\lambda) \cdot L(\lambda) \cdot x_2\} \quad (5)$$

The correction factor $x_1$ takes the measurement geometry and the multiply scattered, unabsorbed, undetected photons into consideration. Measurements errors of the slice thickness d and imprecisions of the reduced scatter coefficient $\mu'_s$ are intended to be compensated by the factor $x_2$. Given knowledge of the absorption coefficients $\alpha_i$, the analytical function according to Equation (5) can be matched to measured in vivo spectra by variation of the concentration $c_i$ of the four tissue components and of the two correction factors $x_1$, $x_2$.

The Absorption Coefficients of the Tissue Components Blood, Water and Fat

For the in vivo measurement of the transmission spectrum of thick biological tissue (d≧3 cm), the principal absorbers blood, water and fat define the diagnostic window. It begins in the short-wave range at about λ=600 nm (blood) and ends in the long-wave range at about λ=1.4 mm (water). Due to the detector system (Si photodiode) employed, however, only measurements in the wavelength range between λ≧650 nm and λ≦1.1 μm were carried out.

FIG. 1 shows the specific absorption coefficients of the blood pigments hemoglobin Hb and oxyhemoglobin HbO in the wavelength range between λ=650 nm and λ=1000 nm. One can clearly see the absorption maximum of Hb at λ=760 nm. The absorption coefficients of Hb and HbO are the same size at the isobestic point (λ=805 nm).

Figure 2:
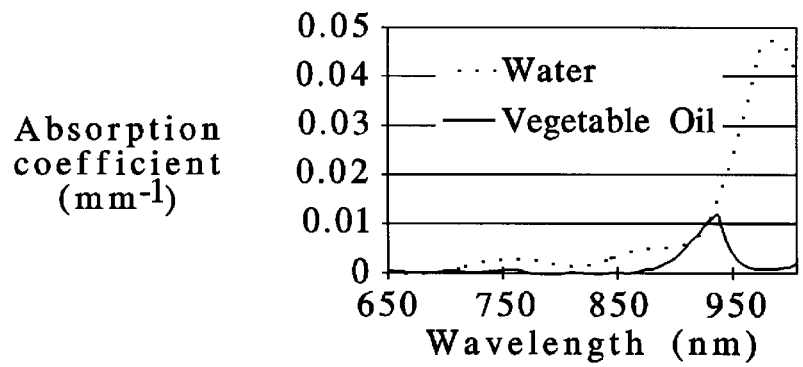

The absorption coefficients respectively calculated from the measured transmission characteristic of water and fat (vegetable oil) are shown in FIG. 2. The O—H resonance of the water molecule has a highly absorbent effect at λ=975 nm. Weaker harmonics of this resonance are observed at λ=840 nm and λ=755 nm. Compared thereto, fat or, respectively, the vegetable oil serving as substitute absorbs especially strongly in the region of the C—H resonance (λ=930 nm). The absorption is considerably weaker in the region of λ=760 and λ≈830 nm, where FIG. 2 exhibits only very flat structures.

The Reduced Scatter Coefficient of the Breast Tissue

Figure 3:
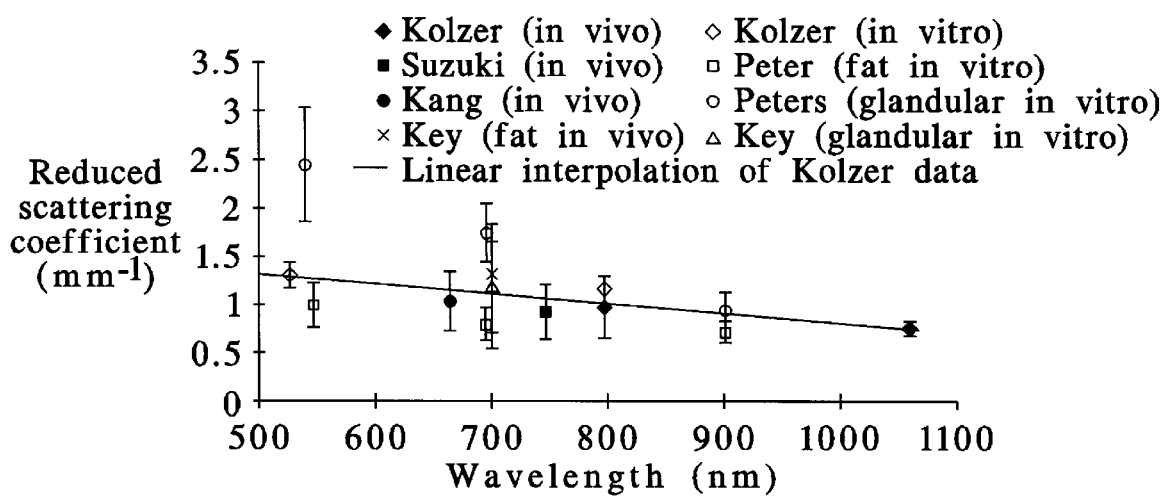
FIG. 3 shows the reduced scatter coefficient of breast tissue (in vivo) dependent on the wavelength.

The calculation of the dependency of the reduced scatter coefficient on the wavelength is only possible given knowledge of the size and composition of the scatter centers. Since corresponding information for the breast tissue are lacking, our own measurements were carried out at various wavelengths. FIG. 3 shows the results of these measurements. The interpolation lines based on the data and the in vivo or, respectively, in vitro measured values of other authors are also shown. The reduced scatter coefficient is only weakly dependent on the wavelength and lies on the order of magnitude of 1 $mm^{-1}$.

Experimental Structure

Figure 4:
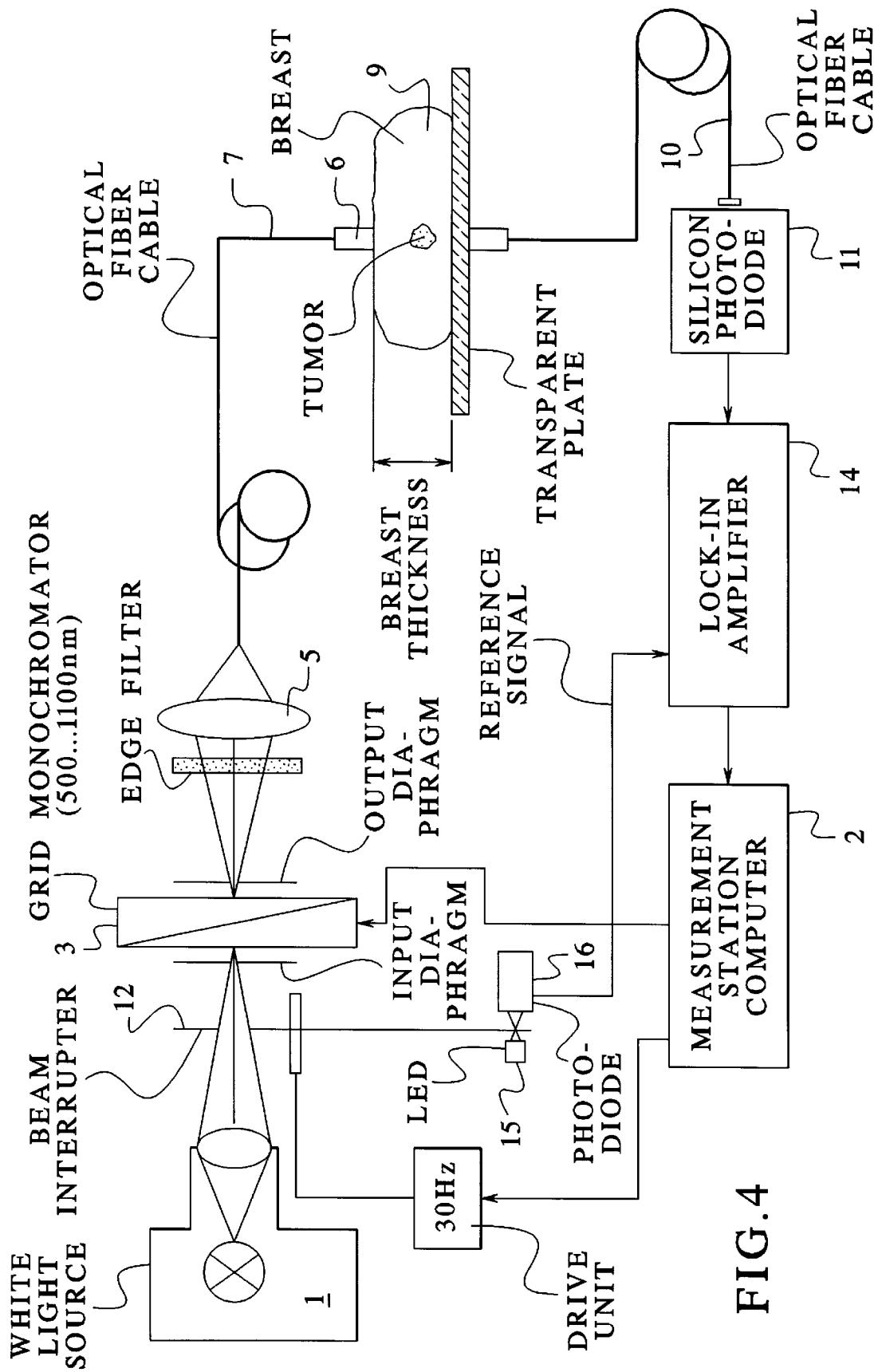
FIG. 4 is a schematic illustration of an apparatus for registering a transmission spectrum according to the method of the invention.

FIG. 4 shows the schematic structure of an apparatus for the registration of an in vivo transmission spectrum. This is thereby essentially a matter of a commercially available spectroradiometer (Merlin, ORIEL Company) whose components were adapted to the new measurement technology. A 100 W halogen lamp 1 that has a uniform and high spectral irradiance in the measurement range (500 nm≦λ≦1100 nm) serves as white light source. Controlled by the computer 2, the grid monochromator 3 (600 lines/mm; linear reciprocal dispersion 12.8 nm/mm at λ=750 nm) resolves the light emitted by the halogen lamp 1 into its spectral components. The selected component subsequently passes through the edge filter 4 arranged following the monochromator 3, so that the optics 5 couples only the radiation diffracted in the first order into the optical fiber cable 7 connected to the fiber head 6 (diameter: 5 mm). Since the radiant intensity at the fiber head amounts to approximately 1 mW (λ=800 nm, width of the monochromator slit s=1 mm), the power density on the skin—at approximately 5 $mW/cm^2$—lies far below the allowable limit value. The radiation penetrates into the breast 9 lying on the transparent plate 8, is absorbed and scattered to a greater or lesser extent according to the optical properties of the transilluminated tissue and in turn emerges at the side lying opposite the optical fiber head 6. An approximately 2 m long optical fiber cable 10 acquires the transmitted radiation and conducts it to the Si photodiode.

The beam interrupter 12 (propeller wheel) arranged in the beam path between the halogen lamp 1 and the monochromator 3 has the job of modulating the intensity of the light entering into the monochromator and, thus, the intensity of the radiation illuminating the breast tissue 9 with a frequency of, for example, f=25 to 30 Hz prescribed by the drive unit 13.

As a result, the output signal of the Si photodiode 11 also has a component exhibiting the modulation frequency f whose amplitude is identified in the lock-in amplifier 14 and read into the computer 2. The forked light barrier composed of a light-emitting diode 15 and a photodiode 16 generates the reference signal adjacent at a second input of the lock-in amplifier 14.

Experimental Results

The in vivo transmission spectra described briefly below were registered with the apparatus shown in FIG. 4. Approximately 150 s are required for the registration of the respectively 50 measured values per spectrum (step width Δλ=10 nm). During the measurement, the widths of the input and output gap of the monochromator 3 were respectively set to 1 mm. This corresponds to a bandwidth of approximately 13 nm, which assures an adequately high spectral resolution. The quantity $$\log\{l(\lambda)/l_0(\lambda)\} \quad (6)$$

referred to below as transmittance was respectively evaluated. It is shown in FIGS. 5 through 8 together with the corresponding simulation curves dependent on the wavelength. A table with the corresponding fit parameters is respectively allocated to the individual spectra. As further parameters, the tables or, respectively, Figures potentially also contain the age of the test subject, particulars about the location of the measurement on the breast and the thickness of the transilluminated tissue.

Despite the differences in the height of the respectively measured transmittance, all in vivo spectra agree in terms of the following features:

1) below $\lambda=600$ nm (blood absorption), the transmittance drops by a number of orders of magnitude;
2) a transmission minimum is observed at approximately $\lambda=760$ nm overlap of the Hb signal and the weaker fat and water signals);
3) more or less pronounced minimums show up at $\lambda=975$ nm (fat) and $\lambda=930$ nm (water);
4) the transmittance decreases within the entire wavelength range with increasing blood content of the tissue.

Figure 5:
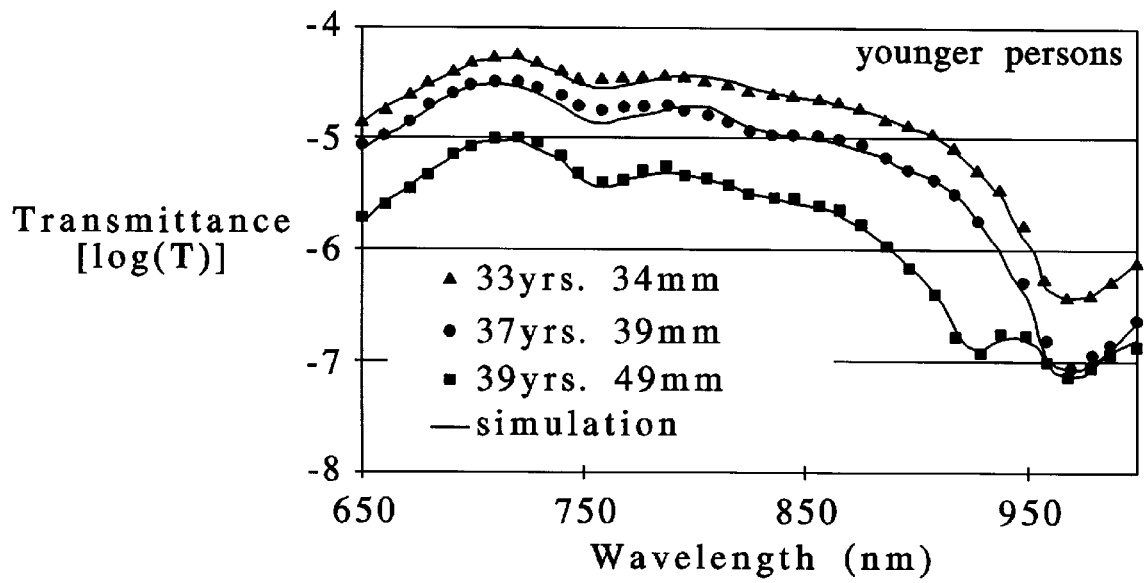
FIGS. 5 through 8 illustrate measured in vivo transmission spectra of a female breast obtained in accordance with the principles of the present invention.
Figure 6:
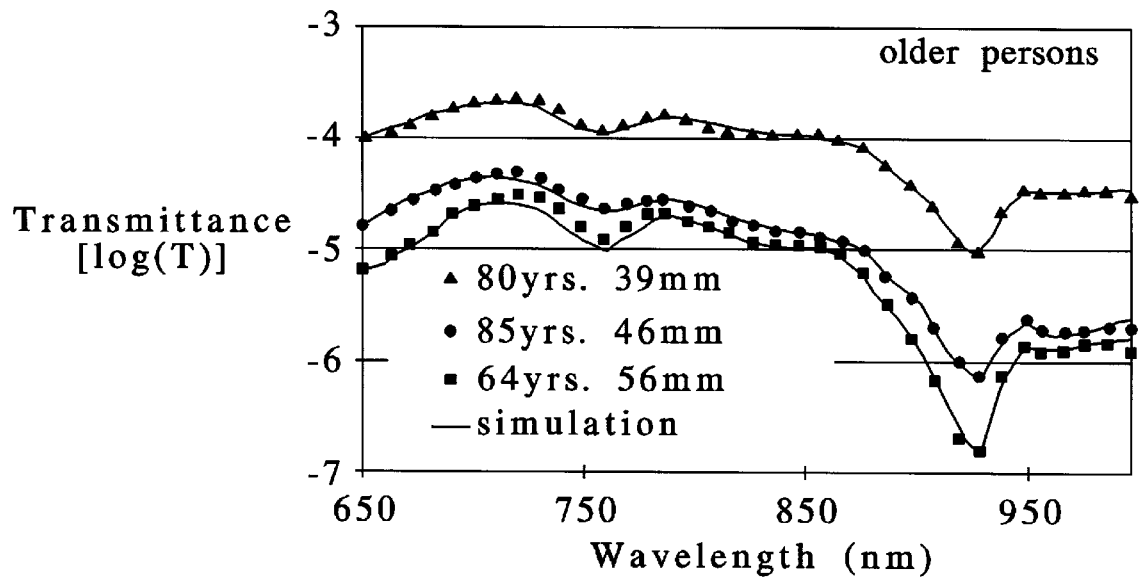

FIGS. 5 and 6 show representative in vivo transmission spectra of the female breast, whereby FIG. 5 is directed to the measurements implemented at younger persons (40 years old and younger) and FIG. 6 is directed to the measurements implemented at older persons (60 years old and older). It is not difficult to see with reference to the fit parameters recited in Table I that younger and older breast tissue differ noticeably from one another with respect to the fat, water and blood content.

TABLE I

| Fit Parameter: | younger persons | | | older persons | | |
|---|---|---|---|---|---|---|
| Age | 39 | 37 | 33 | 85 | 80 | 64 |
| Water [%] | 33 | 65 | 70 | 17 | 11 | 12 |
| Fat [%] | 67 | 35 | 30 | 83 | 89 | 88 |
| Hb [1/min] | 0.0012 | 0.0017 | 0.002 | 0.0005 | 0.0002 | 0.0005 |
| HbO [1/mm] | 0.0042 | 0.0042 | 0.0041 | 0.003 | 0.0014 | 0.0018 |
| $x_1$ | 0.0002 | 0.0005 | 0.0007 | 0.0004 | 0.0006 | 0.0005 |
| $x_2$ | 2.1 | 2.1 | 2.1 | 1.9 | 1.65 | 1.85 |

Figure 7:
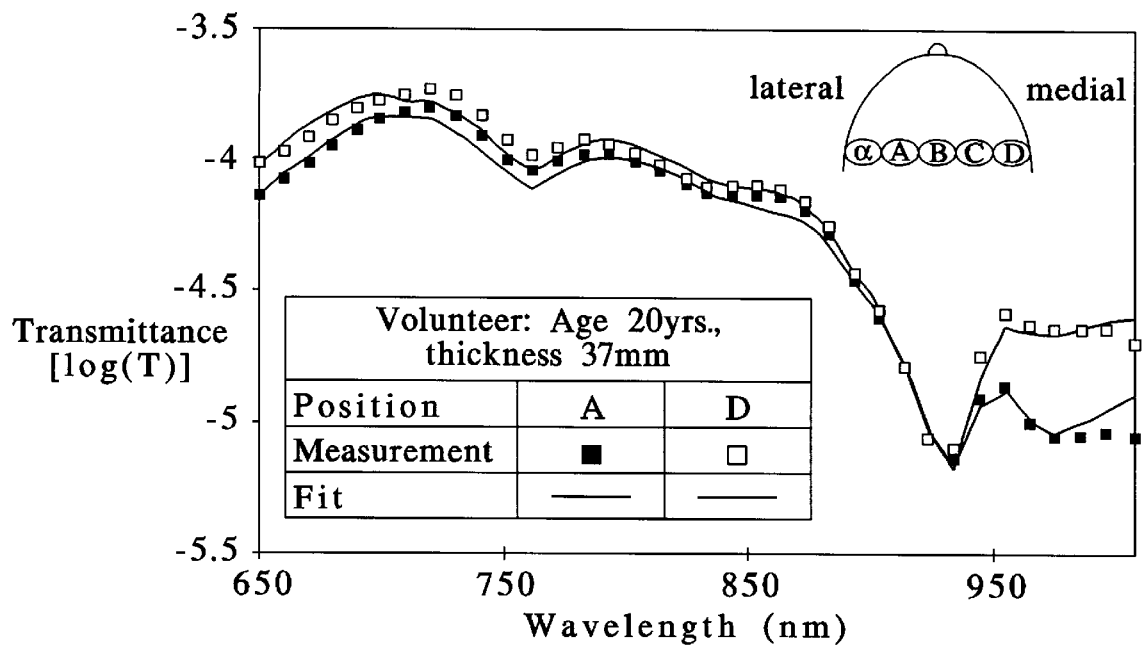

FIG. 7 shows the influence of the measurement position on the in vivo transmission spectrum. Only the spectra measured at the positions "A" and "D" are shown. With the parameters recited in Table II, one again succeeds in describing the spectra very well by the function $l(\lambda)$ recited in Equation (5).

TABLE II

| | Fit Parameter: | | | | |
|---|---|---|---|---|---|
| Position | ref | A | B | C | D |
| Water [%] | 24 | 24 | 20 | 16 | 12 |
| Fat [%] | 76 | 76 | 80 | 84 | 88 |
| Hb [1/mm] | 0.0005 | 0.0005 | 0.0005 | 0.0005 | 0.0003 |
| HbO [1/mm] | 0.0023 | 0.0024 | 0.0024 | 0.0025 | 0.0025 |
| X1 | 0.0006 | 0.0006 | 0.0006 | 0.0006 | 0.0006 |
| X2 | 1.4 | 1.53 | 1.6 | 1.6 | 1.6 |

Figure 8:
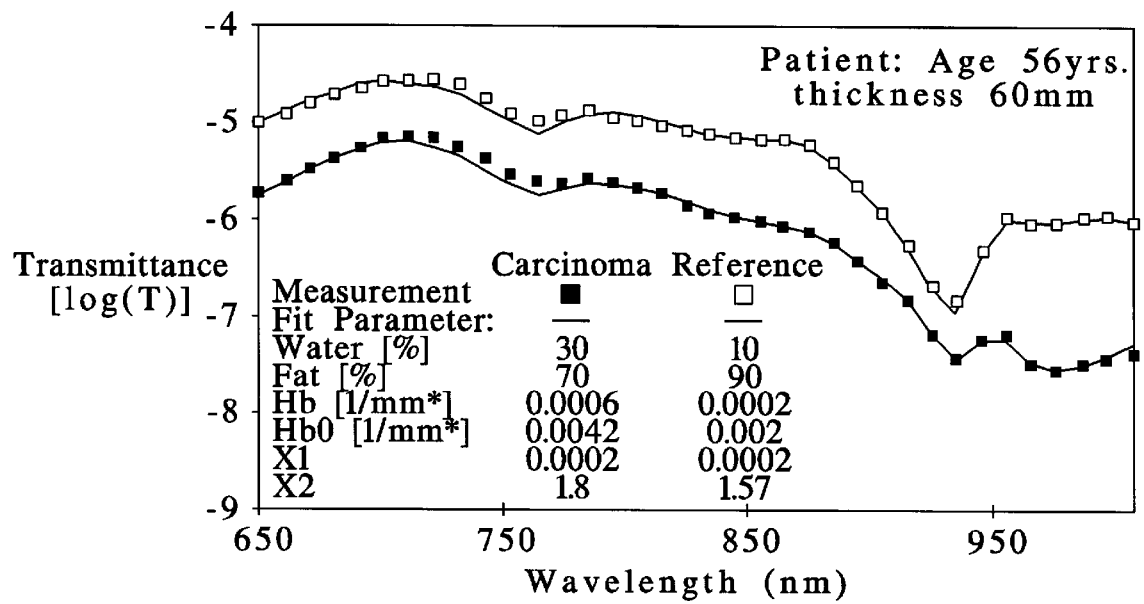

As FIG. 8 shows, the transmission spectrum (black squares) measured at an unhealthy breast (invasive duct carcinoma) differs clearly, particularly in the wavelength range between $\lambda=900$ nm and $\lambda=1000$ nm, from the reference spectrum registered at the corresponding location of the healthy breast (unfilled squares). This can be essentially attributed to the modified water and fat content in the region of the carcinoma compared to the healthy breast. Moreover, the transmittance measured at the unhealthy breast is clearly lower than in the reference spectrum at all wavelengths.

The invention, of course, is not limited to the described exemplary embodiments. Thus, it is possible without difficulty to also register reflection spectra and to again describe these by Equation (5). The quantity $L(\lambda)$ is then established by $$L(\lambda) = \frac{d}{d\mu_a} \ln\left(\frac{R_s(r)}{R(r)}\right) \tag{7}$$

with r: source-detector spacing (see Farell et al., Med. Phys. 19(4)(1992), pp. 879–889).

We claim as our invention:

1. Method for the spectroscopic examination of a biological tissue comprising the steps of:

(a) irradiating a tissue region with non-ionizing radiation having an intensity $l_0(\lambda)$ and a wavelength $\lambda$ while varying said wavelength;

(b) registering a spectrum $l(\lambda)$ from an element selected from the group consisting of a transmission spectrum and a reflection spectrum by an element selected from the group consisting of measuring the intensity of the radiation transmitted by the tissue and radiation reflected by the tissue dependent on the wavelength $\lambda$;

(c) employing an analytical function to approximately describe a quantity from an element selected from the group consisting of said spectrum $l(\lambda)$, said spectrum $l(\lambda)/l_0(\lambda)$ normed to the incident radiation intensity, and $\log\{l(\lambda)/l_0(\lambda)\}$, said analytical function having a Beer-Lambert dependency on a first parameter describing the absorption properties of the tissue and a second parameter representing a slice thickness, the first parameter being dependent on identified concentrations $c_i$ of a plurality i of selected tissue components employed as fit parameters as well as on specific absorption coefficients $\alpha_i(\lambda)$ according to the relationship $$\mu_a(\lambda) = \sum_i c_i \cdot \alpha_i(\lambda).$$

with an average path length $L(\lambda)$ of the photons in the tissue comprising the second parameter; and (d) comparing the identified concentration $c_i$ to reference values.

2. Method according to claim 1, characterized in that the analytical function is established by the equation $$l(\lambda) = l_0(\lambda) \cdot x_1 \cdot \exp\{-\mu_s(\lambda) \cdot L(\lambda) \cdot x_2\}$$

whereby $x_1$, $x_2$ reference wavelength-independent correction factors.

3. Method according to claim 1 wherein the average path length $L(\lambda)$ of the photons in the tissue is dependent on a thickness d of the transilluminated tissue, a reduced scatter coefficient $\mu_s'(\lambda)$ and on the absorption coefficient $\mu_a$ of the tissue according to the relationship $$L = \left(4\frac{\mu_a}{3(\mu_a + \mu'_s)}\right)^{-1/2} \frac{\left(d - \frac{1}{\mu'_s}\right)\exp\left(\frac{2}{\mu'_s}\sqrt{\mu_a 3(\mu_a + \mu'_s)}\right) - \left(d + \frac{1}{\mu'_s}\right)}{\exp\left(\frac{2}{\mu'_s}\sqrt{\mu_a 3(\mu_a + \mu'_s)}\right) - 1}$$

4. Method according to claim 1 wherein the tissue is approximated as a uniform mixture of water, fat, hemoglobin and oxyhemoglobin, whereby volume parts of water and fat supplement to 100%.

5. Method according to claim 1 comprising modulating the intensity of the incident radiation at a modulation frequency and registering an amplitude of an output signal of a detector system exhibiting the modulation frequency dependent on the wavelength.

* * * * *